(12) United States Patent
Litvin et al.

(10) Patent No.: US 9,916,669 B2
(45) Date of Patent: Mar. 13, 2018

(54) PROJECTION DATA CORRECTION AND COMPUTED TOMOGRAPHY VALUE COMPUTATION

(71) Applicant: Analogic Corporation, Peabody, MA (US)

(72) Inventors: Andrew Litvin, Brookline, MA (US); David Lieblich, Worcester, MA (US); Sergey Simanovsky, Brookline, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 200 days.

(21) Appl. No.: 14/833,681

(22) Filed: Aug. 24, 2015

(65) Prior Publication Data
US 2017/0061654 A1 Mar. 2, 2017

(51) Int. Cl.
| | | |
|---|---|---|
| G06T 5/00 | (2006.01) | |
| A61B 6/00 | (2006.01) | |
| G06T 11/00 | (2006.01) | |
| G01N 23/04 | (2018.01) | |
| A61B 6/03 | (2006.01) | |

(52) U.S. Cl.
CPC ............ *G06T 11/006* (2013.01); *A61B 6/032* (2013.01); *A61B 6/482* (2013.01); *G01N 23/046* (2013.01); *G06T 5/002* (2013.01); *G06T 2211/408* (2013.01)

(58) Field of Classification Search
None
See application file for complete search history.

(56) References Cited

U.S. PATENT DOCUMENTS

2007/0237288 A1* 10/2007 Tkaczyk .............. A61B 6/032 378/5
2011/0103542 A1* 5/2011 Allmendinger ........ A61B 6/032 378/4

FOREIGN PATENT DOCUMENTS

| WO | WO2013165396 | * 7/2013 | ............. G06T 11/00 |
|---|---|---|---|
| WO | 2013165396 | 11/2013 | |

OTHER PUBLICATIONS

Gonzales, et al., "Rectangular Fixed-Gantry CT Prototype: Combining CNT X-Ray Sources and Accelerated Compressed Sensing-Based Reconstruction", Access, IEEE , vol. 2, no., pp. 971,981, 2014, http://ieeexplore.ieee.org/stamp/stamp.jsp?tp=&arnumber=6882769.

* cited by examiner

*Primary Examiner* — Utpal Shah
(74) *Attorney, Agent, or Firm* — Cooper Legal Group, LLC

(57) ABSTRACT

Among other things, one or more techniques and/or systems are described for correcting projection data generated from a computed tomography (CT) examination of an object and/or for computing or updating a CT value of the object from the projection data. An image generator is configured to generate a CT image of an object under examination. Using this CT image, a set of actions are performed to correct projection data from which the CT image was generated and/or to update a CT value of one or more voxels within the CT image. In this way, the projection data and/or CT image is adjusted to reduce image artifacts and/or otherwise improve image quality and/or object detection.

20 Claims, 6 Drawing Sheets

PROJECTION DATA CORRECTION AND COMPUTED TOMOGRAPHY VALUE COMPUTATION

BACKGROUND

The present application relates to the field of radiation imaging systems. It finds particular application to correcting projection data generated from a computed tomography (CT) examination of an object and/or for computing CT values of an object or sub-objects thereof from the projection data.

Computed tomography (CT) systems and other radiation imaging modalities, are useful to provide information, or images, of interior aspects of an object under examination. Generally, the object is exposed to radiation comprising photons (e.g., x-rays, gamma rays, etc.), and an image(s) is formed based upon the radiation absorbed and/or attenuated by interior aspects of the object, or an amount of radiation photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

CT systems may be configured as single energy radiation imaging systems or multi-energy (e.g., dual-energy) radiation imaging systems. Although commonly referred to as a single energy radiation system, single energy radiation imaging systems are typically configured to use a single spectrum of radiation photon energy to generate (e.g., reconstruct) an image(s) of an object. Respective voxels of a three-dimensional image produced by a single energy radiation imaging system represent a CT value which is based upon the density of the object represented by the voxel. Multi-energy radiation imaging systems are configured to use multiple, distinct radiation photon energy spectra to generate an image(s) of an object. Respective voxels of a three-dimensional image produced by a multi-energy radiation imaging system may represent a CT value, which is based upon the density of the object represented by the voxel, and/or a z-effective value, which is based upon the atomic composition of the object. To capture data from multiple, distinct energy spectra, the multi-energy radiation imaging system may be configured to emit multiple, distinct energy spectra or the detector array may be configured to filter the impinging radiation photons (e.g., emitted across a single energy spectrum) based upon energy (e.g., dividing an emitted energy spectrum into a plurality of smaller energy spectra).

During generation (e.g., reconstruction) of images produced by single energy radiation imaging systems and/or multi-energy radiation imaging systems, image artifacts may be introduced due to, among other things, inherent phenomena that occur due to the interaction of radiation and objects. For example, radiation interacting with two objects of a same density and atomic composition may scatter differently based upon the shape of respective objects, objects surrounding each object, etc. As another example, objects having a higher density and/or atomic number may reflect or absorb a disproportionate amount of radiation in a low range(s) of the emitted radiation spectrum or spectra. This later phenomenon is sometimes referred to as beam hardening.

Image artifacts may cause an object to appear to have a different density and/or atomic composition than its true density and/or atomic composition. Such differences may result in false positives and/or false negatives during an inspection of the image by personnel and/or by object detection software configured to identify objects of interest (e.g., threat objects, malignant growths, etc.), for example.

SUMMARY

Aspects of the present application address the above matters, and others. According to one aspect, a method for correcting projection data generated from a computed tomography (CT) examination of an object is provided. Projection data of the object is acquired. A CT image of the object is generated based upon the projection data. The CT image is segmented to identify a set of sub-objects within the object. The set of sub-objects comprises a first sub-object and a second sub-object. A first z-effective value is determined for the first sub-object and a second z-effective value is determined for the second sub-object. A beam hardening correction is performed upon the projection data using at least one of the first z-effective value or the second z-effective value to obtain corrected projection data.

According to another aspect, a method for computing a CT value of an object from projection data is provided. A CT image of the object is acquired. The CT image is segmented to identify a sub-object within the object. An initial CT value is determined for the sub-object. The initial CT value for the sub-object is applied to voxels of the CT image to generate a synthetic CT image. The synthetic CT image is forward modeled to generate synthetic CT projection data. The synthetic CT projection data is compared with measured projection data to determine a measure of similarity between a projection value of a ray intersecting the sub-object as represented in the measured projection data and a projection value of the ray as represented in the synthetic CT projection data. The initial CT value for the sub-object is updated when the measure of similarity is below a specified threshold to generate an updated CT value for the sub-object.

According to yet another aspect, a system for correcting projection data generated from a CT examination of an object is provided. The system comprises an image generator configured to reconstruct a CT image of the object based upon projection data of the object and to segment the CT image to identify a set of sub-objects within the object. The set of sub-objects comprises a first sub-object and a second sub-object. The image generator is also configured to determine a first z-effective value for the first sub-object and a second z-effective value for the second sub-object and to perform a beam hardening correction upon the projection data using at least one of the first z-effective value or the second z-effective value to obtain corrected projection data.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

Figure 1:
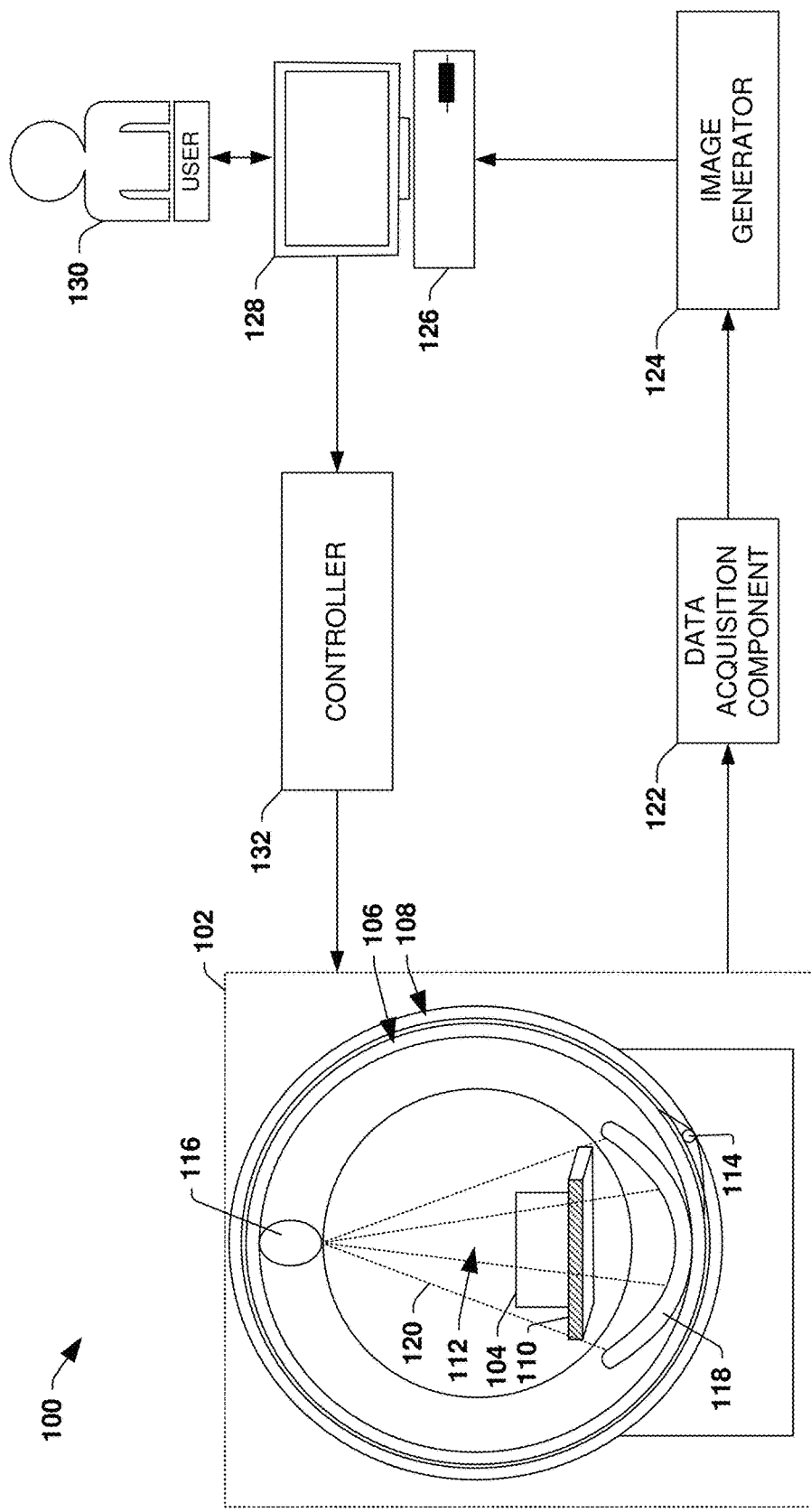
FIG. 1 illustrates an example environment of a radiation imaging system.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Computed tomography (CT) images and other images produced from radiation imaging systems may exhibit image artifacts due to radiation scatter, beam hardening, etc., which may alter a perceived density of an object under examination. That is, in the absence of artifacts, CT values represented within a CT image provide a close correspondence to the physical density of the object. Artifacts in the CT image cause a portion of the object, in a region of the CT image where the artifact is located, to appear to have a density other than its true density.

The degree or severity of such radiation scatter, beam hardening, etc. may be a function of extrinsic properties of an object (e.g., the object's shape, position, orientation, etc.) and other objects surrounding or neighboring the object. Consequently, CT values (e.g., reconstructions of measured attenuation and CT number) of an object can be dispersed over a range of values that are determined by extrinsic properties of the object and its surroundings, rather than true physical density. Thus, discriminating between two objects with relatively similar density values may become more ambiguous because of CT number dispersion, for example.

Accordingly, systems and/or techniques are described herein for adjusting projection values or CT values, within images used to discriminate between objects based upon density, where such adjustments may reduce or eliminate CT number dispersion caused by extrinsic factors. Images that permit discrimination between objects based upon density may be referred to herein as CT images because the coloring or shading of respective voxels is based upon a CT value, which is a function of the density of the object being represented by the voxel.

As will be further described below, a single or multi-energy radiation imaging system (e.g., CT system) may be utilized to acquire projection data of an object. Such projection data may be single energy projection data (e.g., from which CT values can be derived) or multi-energy projection data (e.g. from which both CT values and z-effective values can be derived). Using this projection data, a CT image is generated (e.g., reconstructed) and a series of post-generation processes are performed on the CT image to correct for the CT number dispersions and/or to adjust CT values represented in the CT image.

According to some of embodiments, the projection data corresponds to multi-energy projection data and the series of post-generation processes comprises segmenting the CT image to identify a set of sub-objects within the object (e.g., a set of items within a suitcase). Using the multi-energy projection data, z-effective values may be determined and/or assigned to respective sub-objects within the set, and a beam hardening correction may be performed upon the projection data using the z-effective values. The beam hardening correction uses the z-effective values of sub-objects extending along a radiation ray's path to correct the projection data corresponding to the radiation ray to account for beam hardening that was experienced by the radiation ray. Using this corrected projection data, an updated CT image may be generated.

According to some embodiments, instead of or in addition to determining a z-effective value for respective sub-objects within the set, an initial CT value is assigned to respective sub-objects within the set. Using these initial CT values, a synthetic CT image is generated. The synthetic CT image is forward modeled to generate synthetic CT projection data, and the synthetic CT projection data is compared with measured projection data to determine a measure of similarity (e.g., to determine a degree of similarity between the synthetic CT projection data and the measured projection data). The initial CT value of one or more sub-objects is updated when the measure of similarity is below a specified threshold to generate an updated CT value(s) for the one or more sub-objects. Such a process may be iteratively repeated until stopping criteria have been met (e.g., the measure of similarity exceeds a specified similarity threshold, the number of iterations has exceeded a specified iteration threshold, etc.). In some embodiments, upon the stopping criteria being satisfied, the synthetic CT projection data and/or the synthetic CT image may be transmitted to an object threat detector to analyze characteristics of respective sub-objects (e.g., shape, density, z-effective, etc.) for possible threats. In still other embodiments, the measured projection data may be corrected using the CT values of the sub-objects at the time the stopping criteria has been satisfied to correct the CT values within the measured projection data. Using this corrected projection data, an updated CT image may be generated.

FIG. 1 illustrates an example radiation imaging system 100. In the illustrated embodiment, the radiation imaging system 100 is a computed tomography (CT) system, although the systems and/or techniques described herein may find applicability to other radiation imaging systems where three-dimensional images are generated. Moreover, it may be appreciated that the arrangement of features, inclusion of features and/or exclusion of other features from the example radiation imaging system 100 is not intended to be interpreted in a limiting manner, such as necessarily specifying the location, inclusion, and/or relative position of the features. By way of example, a data acquisition component 122 may be coupled to a rotating gantry 106 and/or embedded within a detector array 118.

The example radiation imaging system 100 comprises an examination unit 102 configured to an examine objects 104. The examination unit 102 comprises a rotating gantry 106 and a stationary support structure 108 (e.g., which may encase and/or surround at least a portion of the rotating gantry 106 (e.g., as illustrated with an outer, stationary ring, surrounding an outside edge of an inner, rotating ring)). The examination unit 102 also comprises a support article 110, such as a bed or conveyor belt, configured to support the object 104 during an examination. In some embodiments, the support article 110 may be configured to translate the object into and/or through an examination region 112 (e.g., a hollow bore in the rotating gantry 106), where the object 104 is exposed to radiation 120, during the examination.

The rotating gantry 106 may surround a portion of the examination region 112 and may comprise a radiation source 116 (e.g., an ionizing radiation source such as an x-ray source or gamma-ray source) and a detector array 118. The detector array 118 is typically mounted on a substantially diametrically opposite side of the rotating gantry 106 relative to the radiation source 116, and during an examination of the object 104, the rotating gantry 106 (e.g., including the radiation source 116 and detector array 118) is rotated about the object 104 by a rotator 114 (e.g., belt, drive shaft, chain, roller truck, etc.). Because the radiation source 116 and the detector array 118 are mounted to the rotating gantry 106, a relative position between the detector array 118 and the radiation source 116 is substantially maintained during the rotation of the rotating gantry 106.

During the examination of the object 104, the radiation source 116 emits cone-beam or fan-beam radiation from a focal spot of the radiation source 116 (i.e., a region within the radiation source 116 from which radiation 120 emanates) into the examination region 112. Such radiation 120 may be emitted substantially continuously and/or may be emitted intermittently (e.g., a brief pulse of radiation 120 is emitted followed by a resting period during which the radiation source 116 is not activated). Further, the radiation 120 may be emitted at a single energy spectrum or multi-energy spectra.

As the emitted radiation 120 traverses the object 104, the radiation 120 may be attenuated (e.g., absorbed and/or scattered) differently by different aspects of the object 104. Because different aspects attenuate different percentages of the radiation 120, the number of photons detected by respective detector cells of the detector array 118 may vary. For example, detector cells that are shadowed by dense aspects of the object 104, such as a bone or metal plate, may detect fewer radiation photons than detector cells that are shadowed by lower density aspects of the object 104, such as skin or clothing, which may allow an overall greater number of radiation photons to pass through and/or may allow a greater percentage of low energy radiation photons to pass through.

The detector array 118 is configured to directly convert (e.g., using amorphous selenium and/or other direct conversion materials) and/or indirectly convert (e.g., using a scintillator and photodetectors and/or other indirect conversion materials) detected radiation into analog signals that can be transmitted from the detector array 118 to a data acquisition component 122 configured to convert the analog signals output by the detector array 118 into digital signals and/or to compile signals that were transmitted within a predetermined time interval, or measurement interval, using various techniques (e.g., integration, photon counting, etc.). Based upon the compiled signals, the data acquisition component 122 can generate projection data indicative of the compiled signals, for example. The projection data can correspond to single energy projection data (e.g., from which CT values can be derived) or multi-energy projection data (e.g., from which CT values and z-effective values can be derived) based upon whether the radiation imaging system 100 is configured as a single energy radiation imaging system or a multi-energy (e.g., dual-energy) radiation imaging system.

The example radiation imaging system 100 further comprises an image generator 124 configured to receive projection data generated by the data acquisition component 122 and to generate image data from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

As will be described in more detail below, as part of an image generation process performed by the image generator 124, the image data and/or data derived from the image data may be processed to correct for CT number dispersions that are present within the image data due to scatter, beam hardening, and/or other phenomenon that occur due to the interaction of radiation with objects. In some embodiments, such image processing may comprise adjusting the projection data, adjusting CT values within CT images produced by the image generator 124 from the projection data, and/or adjusting the CT values associated with one or more sub-objects represented within the CT image(s).

The radiation imaging system 100 also includes a terminal 126, or workstation (e.g., a computer), configured to receive image(s) from the image generator 124, which can be displayed on a monitor 128 to a user 130 (e.g., security personnel, medical personnel, etc.). In this way, the user 130 can inspect the image(s) to identify areas of interest within the object(s) 104. The terminal 126 can also be configured to receive user input which can direct operations of the examination unit 102 (e.g., a speed of gantry rotation, an energy level of the radiation, etc.).

In the example radiation imaging system 100, a controller 132 is operably coupled to the terminal 126. The controller 132 may be configured to control operations of the examination unit 102, for example. By way of example, in some embodiments, the controller 132 may be configured to receive information from the terminal 126 and to issue instructions to the examination unit 102 indicative of the received information (e.g., adjust a speed of a conveyor belt, adjust a voltage applied to the radiation source 116, etc.).

Figure 2:
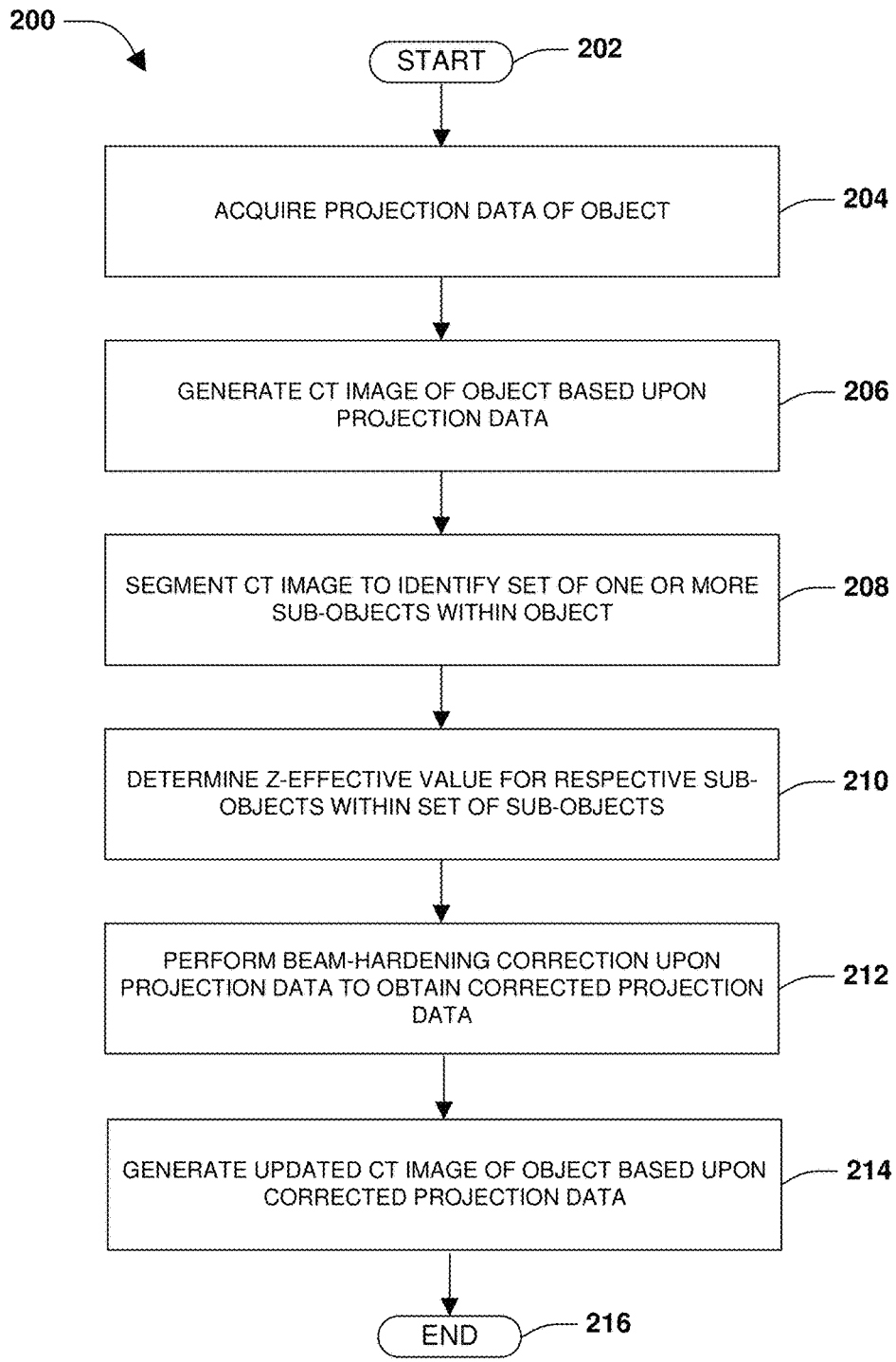
FIG. 2 is a flow diagram illustrating an example method for correcting projection data generated from a computed tomography (CT) examination of an object.

Referring to FIG. 2, a flow diagram of an example method 200 for correcting projection data generated from a computed tomography (CT) examination is provided. In some embodiments, such a method 200 is performed by the image generator 124 as part of an image generation process (e.g., an image reconstruction process) and/or as part of a post image generation process (e.g., a post-reconstruction process).

The example method 200 starts at 202. At 204, projection data of an object is acquired (e.g., from the data acquisition component 122). The projection data can correspond to single energy projection data or multi-energy projection data depending upon whether the radiation imaging system 100 is configured as a single energy radiation imaging system or a multi-energy (e.g., dual-energy) radiation imaging system.

At 206, a CT image of the object is generated (e.g., reconstructed) based upon the projection data. The CT image is a three-dimensional (3D) image and comprises a plurality of voxels respectively representing a portion of the object or a portion of a sub-object comprised within the object. By way of example, in embodiments where the object under examination is a suitcase, voxels in an image produced from an examination of the object may represent various sub-objects within the suitcase (e.g., clothing, books, electronics, etc.). The coloring or shading of respective voxels is a function of a CT value associated with the voxel. The CT value is a function of the density of a sub-object represented by the voxel. Thus, a CT image may, at times, be referred to as a density image.

At 208, the CT image is segmented to identify a set of one or more sub-objects within the object. By way of example, the CT image may be segmented to identify a first sub-object and a second sub-object (e.g., among other sub-objects) within the object. Such segmentation may comprise identifying boundaries between sub-objects and/or edges of sub-objects based upon transitions in CT values between voxels and splitting voxels into groups based upon these boundaries or edges, although other segmentation techniques known to those of skill in the art are also contemplated.

At 210, a z-effective value for respective sub-objects within the set is determined. By way of example, a first z-effective value for the first sub-object and a second z-effective value for the second sub-object may be determined. In some embodiments, determining a z-effective value of a sub-object comprises assuming that the sub-object has a uniform atomic composition and determining, from the multi-energy projection data, a z-effective value for the sub-object based upon a portion of the multi-energy projection data corresponding to radiation rays intersecting the sub-object. In still other embodiments, determining the z-effective value for a sub-object comprises reconstructing a z-effective image from the multi-energy projection data, segmenting the z-effective image to identify a set of sub-objects within the z-effective image, and correlating the set of sub-objects identified within the segmented CT image with the set of sub-objects identified within the segmented z-effective image.

In still another embodiment, the z-effective values of respective sub-objects may be determined according to an approach described in International Application Number PCT/US2012/035984, assigned to Analogic Corporation, which is incorporated herein by reference. According to such an approach, an initial z-effective value for respective sub-objects that are identified from the CT image may be determined at random or based upon a priori knowledge about respective sub-objects, and voxels representing a sub-object may be assigned the initial z-effective value of the sub-object. By way of example, an initial z-effective value for a first sub-object may be applied to voxels of the CT image that are representative of the first sub-object and an initial z-effective value for a second sub-object may be applied to voxels of the CT image that are representative of the second sub-object to generate a z-effective image. The z-effective image may be forward modeled to generate synthetic multi-energy projection data. The synthetic multi-energy projection data may be compared by the image generator 124 to the multi-energy projection data acquired from the data acquisition component 122. The initial z-effective value for one or more sub-objects may be updated based upon results of the comparison. In an example, z-effective values for one or more sub-objects may be iteratively updated based upon comparisons of synthetic multi-energy projection data (e.g., iteratively determined based upon updates to initial z-effective values) and the multi-energy projection data to determine z-effective values for respective sub-objects identified within the CT image during segmentation at 208.

At 212, beam hardening correction may be performed upon the projection data (e.g., the measured projection data) using the z-effective values for respective sub-objects within the set of sub-objects identified within the CT image. By way of example, the beam hardening correction may be performed upon the projection data using at least one of the first z-effective value or the second z-effective value to obtain corrected projection data. The beam hardening correction may comprise a polynomial beam hardening correction or other polynomial function that can be utilized to obtain corrected projection data based upon the z-effective values of one or more sub-objects. In some embodiments, such a polynomial function has one or more polynomial coefficients that are chosen for a specific z-effective value using a calibration procedure, a numerical simulation, a theoretical approach, or other type of beam hardening correction.

In an example of a beam hardening correction, a radiation ray, intersecting the first sub-object and the second sub-object, may be identified. A beam hardening correction parameter may be generated based upon the first z-effective value and/or the second z-effective value. In an example, a first weight for the first z-effective value may be determined based upon a density (e.g., derived from the CT value) of the first sub-object and/or a pass length of the radiation ray through the first sub-object. A second weight for the second z-effective value may be determined based upon a density of the second sub-object and/or a pass length of the radiation ray through the second sub-object. The first weight may be applied to the first z-effective value to obtain a weighted first z-effective value. The second weight may be applied to the second z-effective value to obtain a weighted second z-effective value. The beam hardening correction parameter may be computed based upon the weighted first z-effective value and/or the weighted second z-effective value. A projection value, within the projection data, corresponding to the radiation ray may be corrected based upon the beam hardening correction parameter. In some embodiments, if adjacent radiation rays appear to pass through materials with different z-effective values and thus lead to different polynomial correction coefficients, then a smoothing filter may be applied for the beam hardening correction to reduce discontinuities.

At 214 in the example method 200, an updated CT image of the object is generated (e.g., reconstructed) based upon the corrected projection data. In some embodiments, the updated CT image is generated using a technique similar to the technique utilized to generate the CT image at 206. In other examples, a generation technique (e.g., reconstruction technique) utilized to generate the CT image at 206 may be different than the generation technique utilized to generate the CT image at 214. By way of example, the CT image may be generated utilizing a first reconstruction algorithm and the updated CT image may be generated utilizing a second reconstruction algorithm that may be the same or different than the first reconstruction algorithm. In an example, the second reconstruction algorithm may reconstruct fewer than all voxels in the CT image. For example, the updated CT image may comprise a smaller array of voxels (e.g., 200×150×122 voxels) than an CT image (e.g., 512×512×300 voxels) generated at 206, for example, because portions of the object that are not of interest (e.g., sub-objects having a CT value within a range indicative of air) may be excluded from the updated CT image, for example In some embodiments, prior to outputting the updated CT image to the terminal 126 for display to a user and/or prior to outputting the updated CT image to an object detection component for object detection (e.g., threat detection), the updated CT image may be compared to the CT image generated at 206 to confirm that the updated CT image has a fewer number of artifacts and/or less significant artifacts (e.g., fewer artifacts in a center region of the CT image). In some embodiments, if the results of the comparison indicate that the CT image has fewer artifacts or less significant artifacts, the CT image may be output from the image generator 124. If the results of the comparison indicate that the updated CT image has fewer artifacts or less significant artifacts, the updated CT image may be output from the image generator 124. In still other embodiments, voxels of the CT image and voxels of the updated CT image may be blended to generate a blended CT image that can be output from the image generator 124. In such embodiments, CT values of voxels of the CT image may be weighted relative to CT values of voxels of the updated CT image. Weights may be assigned to CT values of voxels of the CT image relative to CT values of voxels of the updated CT image based upon a measure of confidence in an effectiveness of a generation algorithm (e.g., reconstruction algorithm) used to generate respective CT images, for example.

The example method 200 ends at 216.

Figure 3A:
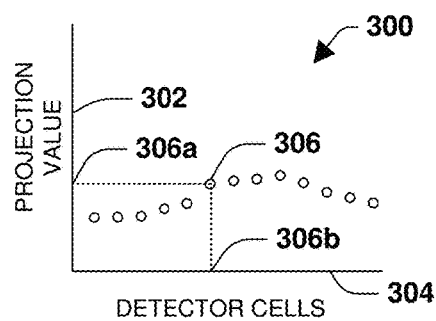
FIG. 3A illustrates an example of projection data.

FIGS. 3A-3F illustrate the correction of projection data using the method 200. FIG. 3A illustrates projection data 300 of an object, such as a suitcase, that may be acquired by the image generator 124 from the data acquisition component 122. The projection data 300 may be represented within a graph having an x-axis 304 representing detector cells of the detector array 118 and a y-axis 302 representing a projection value for the measurement interval (e.g., an amount of charge detected during the measurement interval). A point 306 on the graph corresponds to a projection value of a first detector cell 306b during the measurement interval. Based upon this point 306, the amount of attenuation experienced by a radiation ray traveling along a known path between the radiation source 116 and the detector array 118 can be determined. While information regarding a single radiation ray may not be sufficient to determine the density of respective sub-objects through which the radiation ray traversed while traveling along the known path, using projection data acquired over a plurality of measurement intervals (e.g., views), the density of the respective sub-objects may be estimated during image generation.

Figure 3B:
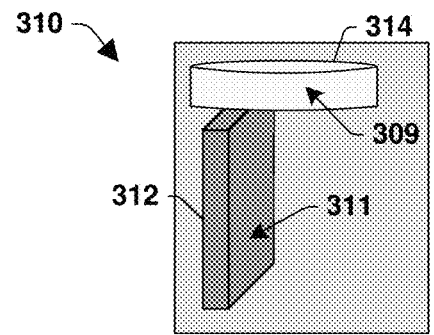
FIG. 3B illustrates an example of a CT image.

FIG. 3B illustrates an example CT image 310 that can been generated at 206 in the example method 200 from the projection data 300. It will be appreciated that for ease of understanding, an outline of the suitcase itself has been removed, as have many of the objects that may be comprised in the suitcase (e.g., such as clothing). Thus, the example CT image 310 merely illustrates two sub-objects. However, it may be appreciated that "background" (e.g., voxels that do not belong to at least one segmented object), such as the voids within a suitcase, may be an extension of object segmentation such as where a CT value and a z-effective value can be assigned to the background (e.g., assignment to the voxels that do not belong to segmented objects). A first sub-object 312 is cube-shaped and has a first density (e.g., as represented by the darker shading 311), and a second sub-object 314 is oval-shaped and has a second density (e.g., as represented by a different, lighter shading 309).

Figure 3C:
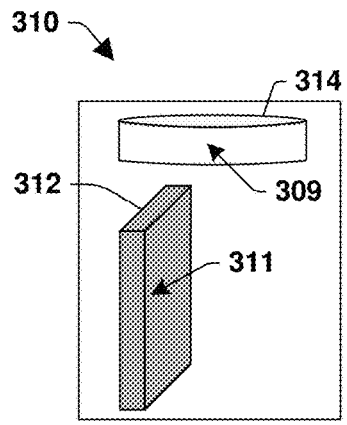
FIG. 3C illustrates an example of a segmented CT image.

FIG. 3C illustrates an example CT image 310 after segmentation at 208 in the example method 200. Segmentation is configured to identify sub-objects within the CT image 310 and to group voxels of the CT image 310 by sub-object. Thus, for purposes of illustration, voxels of the CT image 310 that are associated with the first sub-object 312 are distinguished from voxels that are associated with the second sub-object 314 (e.g., as represented by the separation of the first sub-object 312 from the second sub-object 314).

Figure 3D:
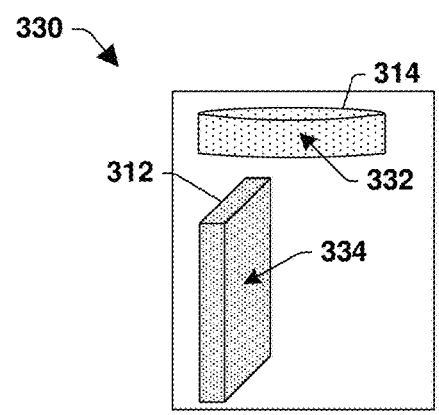
FIG. 3D illustrates an example of a segmented CT image having z-effective values assigned to sub-objects represented therein.

FIG. 3D illustrates an assignment of z-effective values for the first sub-object 312 and the second sub-object 314 within the suitcase based upon a z-effective value for respective sub-objects being determined at 210 in the example method 200. For example, a set of voxels representing the first sub-object 312 may be assigned a first z-effective value (e.g., represented by a first fill pattern 334) and a set of voxels representing the second sub-object 314 may be assigned a second z-effective value (e.g., represented by a second fill pattern 332) to generate a CT z-effective image 330.

Figure 3E:
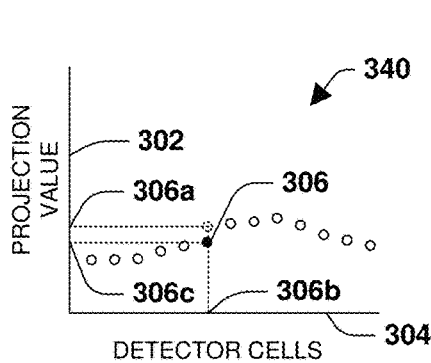
FIG. 3E illustrates an example of corrected projection data.

FIG. 3E illustrates corrected projection data 340, which may be generated at 212 in the example method 200 based upon the z-effective values for the first sub-object 312 and the second sub-object 314 using a beam hardening correction. The beam hardening correction may use a beam hardening correction parameter, derived from the first z-effective value for the first sub-object 312 and the second z-effective value for the second sub-object 314 to correct a projection value (e.g., correct an amount of charge detected by the first detector cell 306b from a first level 306a to a second level 306c) for a radiation ray traversing the first sub-object 312 and the second sub-object 314 and intersecting the first detector cell 306b during the measurement interval.

Figure 3F:
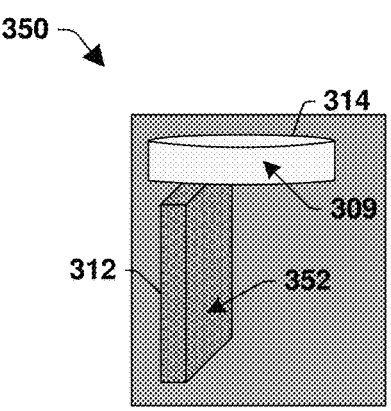
FIG. 3F illustrates an example of an updated CT image.

FIG. 3F is an example updated CT image 350 that can be generated at 214 based upon the corrected projection data 340. It may be appreciated that due to the projection data 340 having been corrected at 212 in the example method 200, the first sub-object 312 may have a different shading 352 than the shading 311 of the first sub-object 312 within the CT image 310 in FIG. 3B. That is, the corrected projection data 340 may result in updated CT values for voxels representing the first sub-object, causing the shading of the first sub-object 312 to change.

Figure 4:
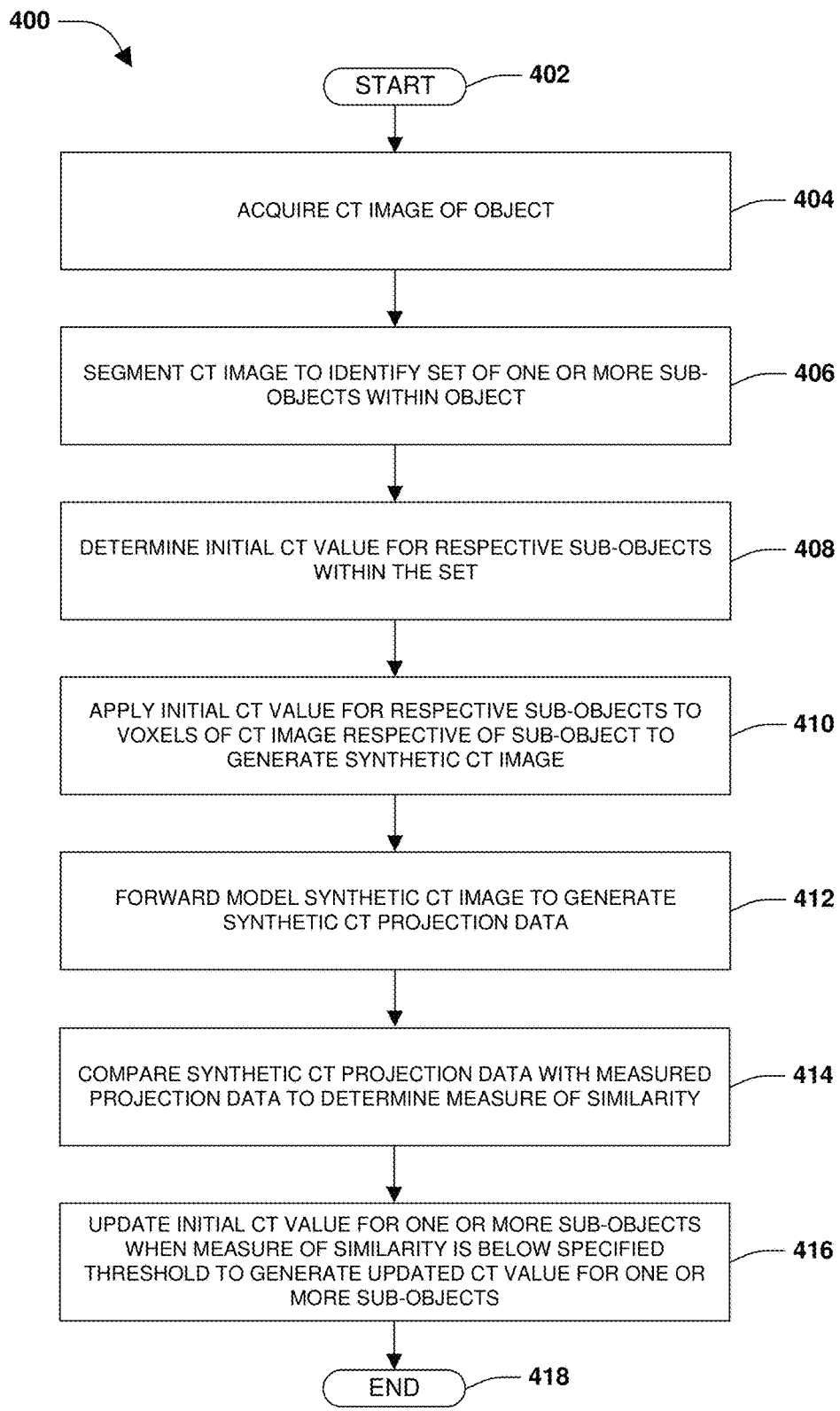
FIG. 4 is a flow diagram illustrating an example method for correcting a CT value of an object from projection data.

Referring to FIG. 4, a flow diagram of an example method 400 for correcting a CT value of an object from projection data generated from a computed tomography (CT) examination is provided. In some embodiments, such a method 400 is performed by the image generator 124 as part of an image generation process (e.g., an image reconstruction process) and/or as part of a post image generation process (e.g., a post-reconstruction process).

The example method 400 starts at 402. At 404, a CT image of the object is acquired and/or generated (e.g., reconstructed). The CT image is a three-dimensional (3D) image and comprises a plurality of voxels respectively representing a portion of the object or a portion of a sub-object comprised within the object. By way of example, in embodiments where the object under examination is a suitcase, voxels in an image produced from an examination of the object may represent various sub-objects within the suitcase (e.g., clothing, books, electronics, etc.). The coloring or shading of respective voxels is a function of a CT value associated with the voxel. The CT value is a function of the density of a sub-object represented by the voxel. Thus, a CT image may, at times, be referred to as a density image.

It may be appreciated that due to, among other things, the CT values of voxels representing a sub-object having a substantially uniform density may have some variation (e.g., CT number dispersion) due to, among other things, radiation scatter, beam hardening, etc.

At 406, the CT image is segmented to identify a set of one or more sub-objects within the object. By way of example, the CT image may be segmented to identify a first sub-object and a second sub-object (e.g., among other sub-objects) within the object. Such segmentation may comprise identifying boundaries between sub-objects and/or edges of sub-objects based upon transitions in CT values between voxels and splitting voxels into groups based upon these boundaries or edges, although other segmentation techniques known to those of skill in the art are also contemplated.

At 408, an initial CT value may be determined for respective sub-objects within the set of one or more sub-objects. That is, it is assumed that respective sub-objects have a uniform density and a single CT value is determined (e.g., chosen using a specified method) for the sub-object. In some embodiments, the CT value that is determined at 408 for a sub-object is an average of the CT values for one or more voxels that represent the sub-object. In some embodiments, the CT value that is determined at 408 is a weighted average of the CT values for one or more voxels that represent the sub-object. By way of example, the CT values of voxels representing a center of the sub-object may be weighted higher in the average than CT values of voxels representing edges of the sub-object. In still other embodiments, a priori information about the sub-object may be used to determine an initial CT value for the sub-object. Such a priori information may comprise z-effective information about the sub-object, geometric information about the sub-object, and/or an environment at least partially surrounding the sub-object. In still other embodiments, an initial CT value for one or more sub-objects within the set may be selected at random and/or according to a specified CT value determination scheme. In still other embodiments, the initial CT value may be determined based upon a weight applied to a central interior region, different than a region near a boundary and intervening region, based upon a size, shape, and/or orientation of the object relatively to a beam.

At 410, the initial CT value for respective sub-objects is applied to voxels of the CT image representative of the sub-object to generate a synthetic CT image. By way of example, an initial CT value for a first sub-object is applied to voxels of the CT image representative of the first sub-object and an initial CT value for a second sub-object is applied to voxels of the CT image representative of the second sub-object. In this way, by applying the initial CT value for a sub-object to voxels of the CT image representative of the sub-object, voxels representative of a sub-object have a uniform CT value, for example.

At 412 in the example method 400, the synthetic CT image is forward modeled (e.g., forward projected) to generate CT projection data. In this way, the synthetic CT image, in image space, is converted to projection data, in projection space (e.g., sinogram space). It may be appreciated that numerous techniques are known in the art for forward modeling CT images and are contemplated for use in forward projecting the synthetic CT image.

At 414, the synthetic CT projection data is compared with the measured projection data used to generate the CT image acquired at 404 to determine a measure of similarity. In some embodiments, the measure of similarity is an average similarity (e.g., or weighted average) between projection values of the synthetic CT projection data and corresponding projection values of the measured projection data. By way of example, a projection value of a first radiation ray represented in the measured projection data may be compared to a projection value of the first radiation ray represented in the synthetic CT projection data to determine a degree of similarity between these two projection values. Further, a projection value of a second radiation ray represented in the measured projection data may be compared to a projection value of the second radiation ray represented in the synthetic CT projection data to determine a degree of similarity between these two projection values. Such a process may be repeated for a plurality of radiation rays and the degree of similarity may be averaged or otherwise combined to determine the measure of similarity between the synthetic CT projection data and the measured projection data.

At 416, the initial CT value for one or more sub-objects may be updated when the measure of similarity is below a specified threshold to generate an updated CT value for the one or more sub-objects. The initial CT value for the one or more sub-objects may be updated based upon the location and/or magnitude of differences between projection values in the measured projection data and the projection values in the synthetic CT projection data.

In an example, the initial CT value may be iteratively updated using the foregoing method based upon comparisons of synthetic CT projection data (e.g., iteratively determined from updated CT values) and the measured projection data. In this way, the CT values for voxels representing various sub-objects (e.g., and thus the CT values for the sub-objects themselves) may be adjusted until the synthetic CT projection data approximates the measured projection data and/or until some other stopping criteria has been satisfied.

At 418, the method 400 ends when specified stopping criteria for halting the iterations has been satisfied.

It will be appreciated that the synthetic CT image may be forward modeled along one or more axes, and thus the scope of the instant application is not limited to forward modeling the synthetic CT image along a single axis. By way of example, the synthetic CT image generated at 410 may be forward modeled along a first set of one or more axes to generate first synthetic CT projection data and may be forward modeled along a second set of one or more axes to generate second synthetic CT projection data. Moreover, the measured projection data to which the synthetic CT projection data is compared corresponds to measured projection data representative of a similar orientation of the object as the synthetic CT projection data. Thus, the first synthetic CT projection data is compared to a first portion of the measured projection data and the second synthetic CT projection data is compared to a second portion of the measured projection data.

In embodiments where the synthetic CT image is forward modeled along two or more sets of axes, the updated CT value may be based upon a measure of similarity corresponding to a degree of similarity between the first portion of the measured projection data and the first synthetic CT projection data and a second measure of similarity corresponding to a degree of similarity between the second portion of the measured projection data and the second synthetic CT projection data. In some embodiments, an impact (e.g., weight) of the measure of similarity on the updating relative to an impact of the second measure of similarity on the updating may be based upon a raw data noise variance, object edge information, and/or whether the projection data corresponds to a ray that has traversed a metal material, for example.

Figure 5A:
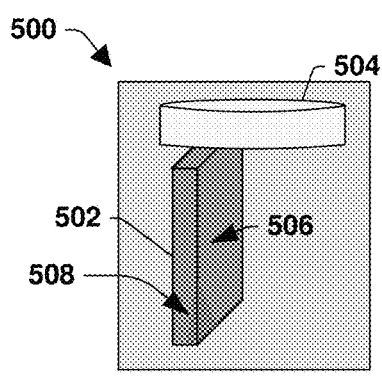
FIG. 5A illustrates an example of a CT image.

FIGS. 5A-5E illustrate the correction of projection data and/or the correction of CT values of an object or sub-objects thereof using the method 400. FIG. 5A illustrates an example CT image 500 of an object such a suitcase under examination by an examination unit 102. It will be appreciated that for ease of understanding, an outline of the suitcase itself has been removed, as has many of the objects that may be comprised in the suitcase (e.g., such as clothing). Thus, the example CT image 500 merely illustrates two sub-objects. A first sub-object 502 is cube-shaped and a second sub-object 504 is oval-shaped. It may be appreciated that the first sub-object 502 may experience CT number dispersion due to radiation scatter, beam hardening, etc. Accordingly, voxels representing a first portion 506 of the first sub-object 502 may have a different CT value than voxels representing a second portion 508 of the first sub-object 502, causing variations in the shading of the first sub-object 502 (e.g., as illustrated by the first portion 506 of the first sub-object 502 being shaded with a lighter color than the second portion 508 of the first sub-object 502.

Figure 5B:
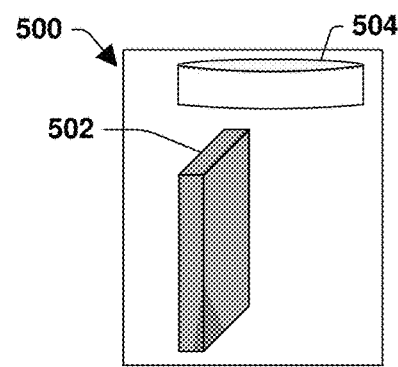
FIG. 5B illustrates an example of a segmented CT image.

FIG. 5B illustrates an example CT image 500 after segmentation at 406 in the example method 400. Segmentation is configured to identify sub-objects within the CT image 500 and to group voxels of the CT image 500 by sub-object. Thus, for purposes of illustration, voxels of the CT image 500 that are associated with the first sub-object 502 are distinguished from voxels that are associated with the second sub-object 504 (e.g., as represented by the separation of the first sub-object 502 from the second sub-object 504). In some embodiment, a CT image that has been segmented is referred to as a segmented CT image.

Figure 5C:
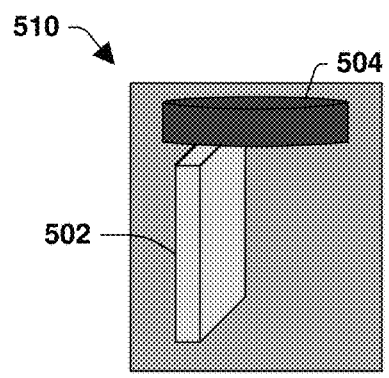
FIG. 5C illustrates an example of a synthetic CT image.

FIG. 5C illustrates a synthetic CT image 510 that is generated at 410 in the example method 400 based upon determining an initial CT value for respective sub-objects at 408 and applying the initial CT value of respective sub-objects to corresponding voxels at 410. It may be appreciated that in the instant example, the shading of the second sub-object 504 in the synthetic CT image 510 is nearly the same as the shading of the second sub-object 504 in the CT image 500. In some embodiments, this may be because the second sub-object 504 experienced little to no CT number dispersion (e.g., and thus respective voxels of the CT image 500 that represent the second sub-object 504 have very little deviation in CT values). It may also be appreciated that in the instant example, the shading of the first sub-object 502 in the synthetic CT image 510 is similar to the shading of a majority of the first sub-object 502 as depicted in the CT image 500. Such a scenario may occur, for example, where the CT values of respective voxels of the CT image 500 representing the first sub-object 502 are averaged to determine an initial CT value for the first sub-object 502.

Figure 5D:
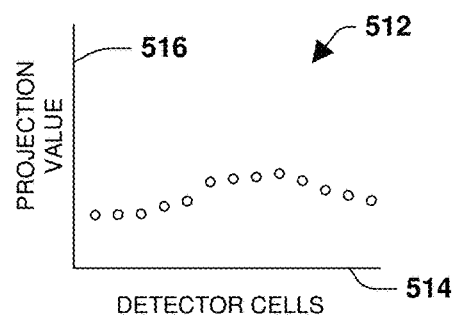
FIG. 5D illustrates an example of synthetic CT projection data.

FIG. 5D illustrates an example of synthetic CT projection data 512 that may be generated at 414 responsive to forward modeling the synthetic CT image 510. The synthetic CT projection data 512 may be represented within a graph having an x-axis 514 representing detector cells of the detector array 118 and a y-axis 516 representing projection values (e.g., an amount of charge expected to be detected by a detector cell during a view represented by the synthetic CT projection data 512).

Figure 5E:
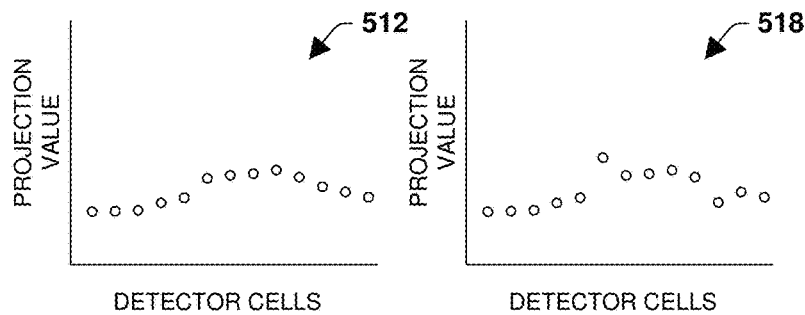
FIG. 5E illustrates an example of a comparison between synthetic CT projection data and measured projection data.

As illustrated at FIG. 5E, the synthetic CT projection data 512 is compared to measured projection data 518 corresponding to the view to determine a degree of similarity between the synthetic CT projection data 512 and the measured projection data 518. If the degree of similarity exceeds a specified similarity threshold, the method 400 ends. If the degree of similarity does not exceed the specified similarity threshold, the CT value assigned to one or more sub-objects may be updated and applied to voxels corresponding to the one or more sub-objects to generate an updated synthetic CT image. The updated synthetic CT image may be forward modeled to generate updated synthetic CT projection data, which may be compared to the measured projection data to determine a degree of similarity. Such a process may be repeated until a specified stopping criteria has been satisfied.

It may be appreciated that features of the example method 200 and features of the example method 400 may be combined to further process images and/or portions thereof. By way of example, the projection data acquired at 204 in the method 200 may be the synthetic CT projection data generated at 412 in the method 400, the CT image generated at 206 in the method 200 may correspond to the synthetic CT image generated at 410 in the example method 400, the CT image acquired at 404 in the example method 400 may correspond to the updated CT image generated at 214 in the example method 200, etc.

Figure 6:
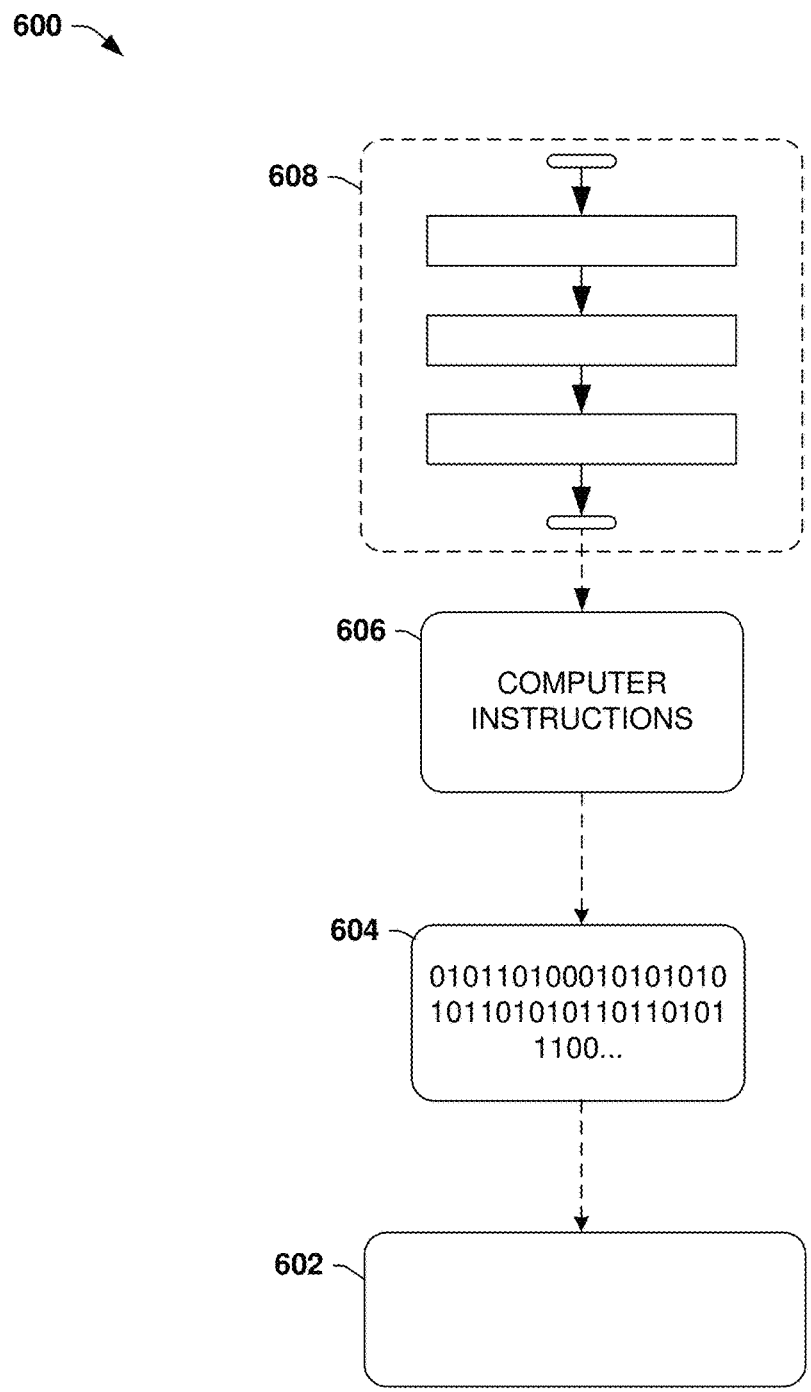
FIG. 6 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 6, wherein the implementation 600 comprises a computer-readable medium 602 (e.g., a flash drive, CD-R, DVD-R, application-specific integrated circuit (ASIC), field-programmable gate array (FPGA), a platter of a hard disk drive, etc.), on which is encoded computer-readable data 604. This computer-readable data 604 in turn comprises a set of processor-executable instructions 606 configured to operate according to one or more of the principles set forth herein. In one such embodiment 600, the processor-executable instructions 606 may be configured to perform a method 608 when executed via a processing unit, such as at least some of the example method 200 of FIG. 2 and/or at least some of the example method 400 of FIG. 4. In another such embodiment, the processor-executable instructions 606 may be configured to implement a system, such as at least some of the example system 100 of FIG. 1. Many such computer-readable media may be devised by those of ordinary skill in the art that are configured to operate in accordance with one or more of the techniques presented herein. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". The claimed subject matter may be implemented as a method, apparatus, or article of manufacture (e.g., as software, firmware, hardware, or any combination thereof).

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method for correcting projection data generated from a computed tomography (CT) examination of an object, comprising:
    acquiring the projection data of the object;
    generating a CT image of the object based upon the projection data;
    segmenting the CT image to identify a set of sub-objects within the object, wherein the set of sub-objects comprises a first sub-object and a second sub-object;
    determining a first z-effective value for the first sub-object and a second z-effective value for the second sub-object; and
    performing a beam hardening correction upon the projection data using at least one of the first z-effective value or the second z-effective value to obtain corrected projection data.

2. The method of claim 1, comprising:
    generating an updated CT image of the object based upon the corrected projection data.

3. The method of claim 2, the generating a CT image comprising generating the CT image utilizing a first reconstruction algorithm and the generating an updated CT image comprising generating the updated CT image utilizing a second reconstruction algorithm different than the first reconstruction algorithm.

4. The method of claim 1, comprising:
    assigning a background CT value to one or more voxels of the CT image that do not represent at least one object within the set of sub-objects.

5. The method of claim 2, comprising:
    comparing the CT image with the updated CT image; and
    generating a blended CT image of the CT image and the updated CT image based upon results of the comparing the CT image with the updated CT image.

6. The method of claim 2, comprising:
    segmenting the updated CT image to identify a second set of sub-objects, wherein the second set of sub-objects comprise a third sub-object and a fourth sub-object;
    determining an initial CT value for the third sub-object and an initial CT value for the fourth sub-object;
    applying the initial CT value for the third sub-object to voxels of the updated CT image representative of the third sub-object and the initial CT value for the fourth sub-object to voxels of the updated CT image representative of the fourth sub-object to generate a synthetic CT image;
    forward modeling the synthetic CT image to generate synthetic CT projection data;
    comparing the synthetic CT projection data to the corrected projection data; and
    updating at least one of the initial CT value for the third sub-object or the initial CT value for the fourth sub-object based upon results of the comparing.

7. The method of claim 1, the beam hardening correction comprising:
    identifying a ray intersecting the first sub-object and the second sub-object;
    generating a beam hardening correction parameter based upon at least one of the first z-effective value or the second z-effective value; and
    correcting a projection value, within the projection data, for the ray based upon the beam hardening correction parameter.

8. The method of claim 7, the generating a beam hardening correction parameter comprising:
    determining a first weight for the first z-effective value based upon at least one of a density of the first sub-object or a pass length of the ray through the first sub-object;

determining a second weight for the second z-effective value based upon at least one of a density of the first sub-object or a pass length of the ray through the first sub-object;

applying the first weight to the first z-effective value to obtain a weighted first z-effective value; and applying the second weight to the second z-effective value to obtain a weighted second z-effective value, wherein the beam hardening correction parameter is computed based upon at least one of the weighted first z-effective value or the weighted second z-effective value.

9. The method of claim 1, the determining a first z-effective value for the first sub-object and a second z-effective value for the second sub-object comprising:

determining an initial z-effective value for the first sub-object and an initial z-effective value for the second sub-object;

applying the initial z-effective value for the first sub-object to voxels of the CT image representative of the first sub-object and the initial z-effective value for the second sub-object to voxels of the CT image representative of the second sub-object to generate a z-effective image;

forward modeling the z-effective image to generate synthetic multi-energy projection data;

comparing the synthetic multi-energy projection data to the projection data; and updating at least one of the initial z-effective value for the first sub-object and the initial z-effective value for the second sub-object based upon results of the comparing.

10. The method of claim 1, the performing beam hardening correction comprising:

utilizing a polynomial function to obtain the corrected projection data.

11. A system for correcting projection data generated from a computed tomography (CT) examination of an object, comprising:

an image generator configured to:
generate a CT image of the object based upon projection data of the object;
segment the CT image to identify a set of sub-objects within the object, where the set of sub-objects comprises a first sub-object and a second sub-object;
determine a first z-effective value for the first sub-object and a second z-effective value for the second sub-object; and
perform a beam hardening correction upon the projection data using at least one of the first z-effective value or the second z-effective value to obtain corrected projection data.

12. A method for correcting projection data generated from a computed tomography (CT) examination of an object, comprising:

segmenting a CT image to identify a first sub-object within an object under examination;
determining a first z-effective value for the first sub-object; and performing a beam hardening correction upon projection data from which the CT image was generated to obtain corrected projection data, comprising:
calculating a first weight as a function of a pass length, through the first sub-object, of a ray;
applying the first weight to the first z-effective value to obtain a weighted first z-effective value;
computing a beam hardening correction parameter based upon the weighted first z-effective value; and
correcting a projection value corresponding to the ray based upon the beam hardening correction parameter.

13. The method of claim 12, wherein:
the segmenting comprises segmenting the CT image to identify a second sub-object intersected by the ray,
the determining comprises determining a second z-effective value for the second sub-object,
the calculating comprises calculating a second weight as a function of a pass length, through the second sub-object, of the ray,
the applying comprises applying the second weight to the second z-effective value to obtain a weighted second z-effective value, and
the computing comprises computing the beam hardening correction parameter based upon the weighted second z-effective value.

14. The method of claim 12, comprising:
generating an updated CT image of the object based upon the corrected projection data.

15. The method of claim 14, comprising:
blending one or more voxels of the CT image with one or more voxels of the updated CT image.

16. The method of claim 12, comprising:
reconstructing the CT image from the projection data.

17. The method of claim 12, wherein the performing comprises:
utilizing a polynomial function to obtain the corrected projection data.

18. The method of claim 12, wherein the determining comprises:
generating a z-effective image from the projection data; and
segmenting the z-effective image to identify the first sub-object.

19. The method of claim 18, wherein:
the segmenting a CT image comprises segmenting the CT image to identify a first set of sub-objects,
the segmenting the z-effective image comprises segmenting the CT image to identify a second set of sub-objects, and
the determining comprises correlating the first set of sub-objects with the second set of sub-objects.

20. The method of claim 12, comprising:
using the projection data to generate the CT image and a z-effective image; and
determining the first z-effective value from the z-effective image.

* * * * *